US00PP26467P3

(12) United States Plant Patent
Van Swieten

(10) Patent No.: US PP26,467 P3
(45) Date of Patent: Mar. 8, 2016

(54) *PHALAENOPSIS* ORCHID PLANT NAMED 'PHALDANXOK'

(50) Latin Name: ***Phalaenopsis* Blume**
Varietal Denomination: PHALDANXOK

(71) Applicant: ANTHURA B.V., Bleiswijk (NL)

(72) Inventor: Martinus Nicolaas Gerardus Van Swieten, The Hague (NL)

(73) Assignee: ANTHURA B.V., Bleiswijk (NL)

( * ) Notice: Subject to any disclaimer, the term of this patent is extended or adjusted under 35 U.S.C. 154(b) by 120 days.

(21) Appl. No.: 14/120,238

(22) Filed: May 9, 2014

(65) Prior Publication Data

US 2015/0327422 P1 Nov. 12, 2015

(51) Int. Cl.
*A01H 5/00* (2006.01)

(52) U.S. Cl.
USPC ..... Plt./311

(58) Field of Classification Search
USPC ..... Plt./311
See application file for complete search history.

(56) References Cited

PUBLICATIONS

PLUTO Plant Variety Database Oct. 22, 2015. p. 1.*

* cited by examiner

*Primary Examiner* — Annette Para
(74) *Attorney, Agent, or Firm* — Jondle & Associates, P.C.

(57) ABSTRACT

A new and distinct variety of *Phalaenopsis* plant named 'PHALDANXOK', particularly characterized by lilac flowers, 2 peduncles, inflorescence that is long and moderate, lanceolate shaped leaves, and propagated by tissue culture is disclosed.

2 Drawing Sheets

Genus and species: *Phalaenopsis* Blume.
Variety denomination: 'PHALDANXOK'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALDANXOK'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes or panicle, often with many showy flowers which open in succession beginning with the lowermost. The flowers possess three sepals and three petals; the lateral ones being alike. The lowermost petals, called the labellum, is three-lobed and is often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* 'PHALDANXOK' is particularly characterized by its attractive and unique lilac flowers, economical propagation by tissue culture, rapid growth, and a plant dimension suitable for packaging and shipping to the market.

'PHALDANXOK' is a product of a planned breeding program conducted in Bleiswijk, The Netherlands.

The new *Phalaenopsis* 'PHALDANXOK' originated from a cross made in February 2002 in Bleiswijk, The Netherlands. The female parent is a pink *Phalaenopsis* pot plant named '07904-0009' (unpatented), while the male parent is a white *Phalaenopsis* pot plant named '05174-0001' (unpatented). A single plant was selected in March 2007 and has been asexually reproduced repeatedly by tissue culture in Bleiswijk, The Netherlands over a 4-year period. The new variety has been found to retain its distinctive characteristics through successive asexual propagations.

Asexual reproduction of 'PHALDANXOK' by tissue culture was first performed in July 2010 in Bleiswijk, The Netherlands and has demonstrated that the new cultivar is firmly fixed and retained through successive generations of asexual reproduction.

Plant Breeder's Rights for this variety have been applied for in Europe on Sep. 20, 2013. 'PHALDANXOK' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) Lilac flowers;
2) 2 peduncles;
3) Inflorescence is long and moderate;
4) The shape of the leaf is lanceolate; and
5) Plants are propagated by tissue culture.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs are of a 50-week old plant grown in a greenhouse in Bleiswijk, The Netherlands in March 2014.

DESCRIPTION OF THE NEW VARIETY

Figure 1:
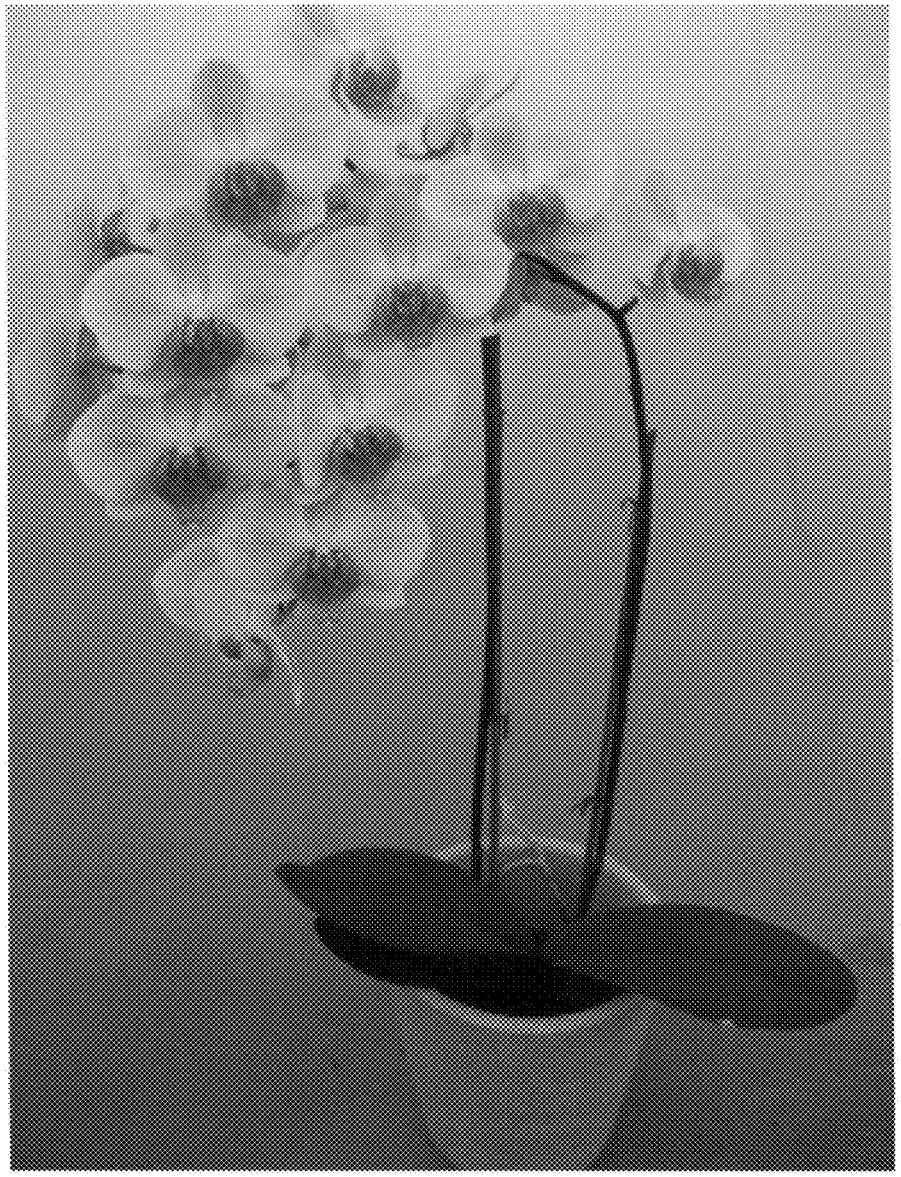
FIG. 1 shows the overall plant habit, including blooms, buds and foliage of 'PHALDANXOK'.
Figure 2:
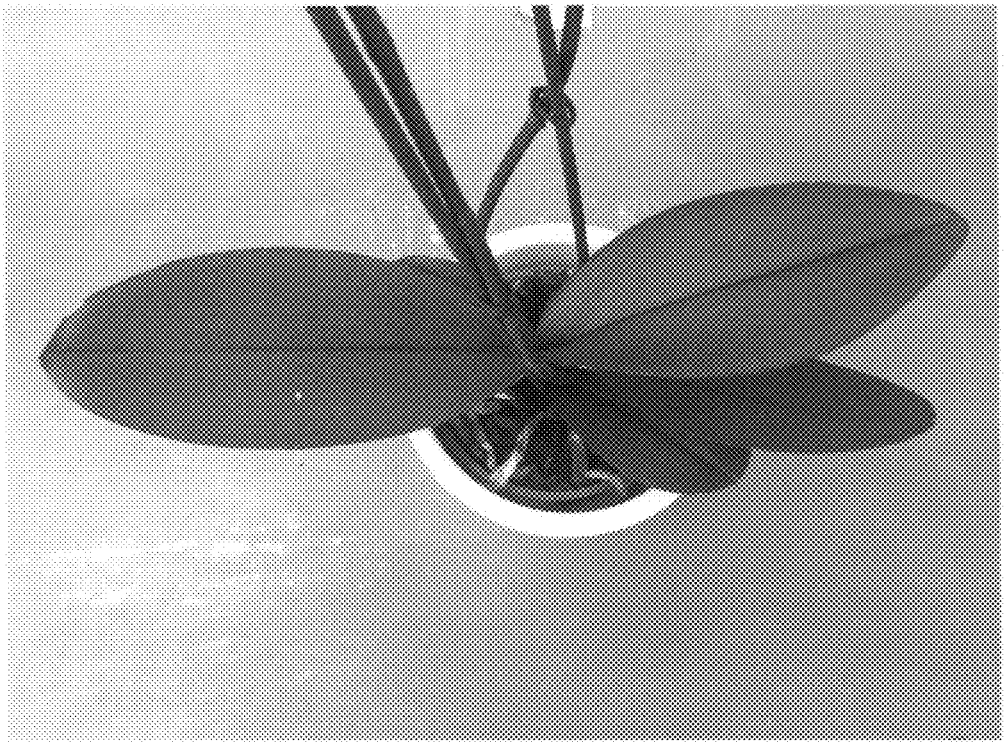
FIG. 2 shows a close-up of the leaves of 'PHALDANXOK'.

The following detailed description sets forth the distinctive characteristics of 'PHALDANXOK'. The data which define these characteristics were collected from asexual reproductions carried out in Bleiswijk, The Netherlands. The plant history was taken on 50-week old plants which were planted from tissue culture in 12 centimeter pots and grown in a greenhouse between 27° C. to 29° C. for 30 weeks, continued by a cooling period of 8 weeks between 18° C. to 20° C. and 12 weeks in a greenhouse of 21° C. Observations were made in March 2014. Color readings were taken under 4-6000 lux natural light in the greenhouse. Color references are primarily to The R.H.S. Colour Chart of The Royal Horticultural Society of London (R.H.S.) (2001).

DETAILED BOTANICAL DESCRIPTION

Classification:
- *Family.*—Orchidaceae.
- *Botanical.*—*Phalaenopsis* Blume.
- *Common name.*—*Phalaenopsis.*
- *Variety name.*—'PHALDANXOK'.

Parentage:
- *Female parent.*—*Phalaenopsis* cultivar '07904-0009' (unpatented).
- *Male parent.*—*Phalaenopsis* cultivar '05174-0001' (unpatented).

Propagation:
- *Type.*—Tissue culture.

Plant:
- *Crop time* (*time to produce a finished flowering plant*).—48 to 50 weeks for a 12 cm pot.
- *Growth habit of inflorescence.*—Standard, green leaves, raceme to panicle.
- *Height* (*including pot, including inflorescence*).—60.0 cm to 70.0 cm.
- *Width* (*measured from leaf tips*).—30.0 cm to 35.0 cm.
- *Vigor.*—Moderate.

Roots:
- *Root description.*—Grey-green-colored roots with light branching lateral roots having grey-green-colored root tips.

Leaves:
- *Mature leaves.*—Quantity per plant: 6 to 7 leaves are produced before flowering. Length (fully expanded): 17.0 cm to 20.0 cm. Width: 7.0 cm to 8.0 cm. Shape: Lanceolate. Apex: Slightly unequal acute. Leaf blade angle with the petiole: Between 15 degrees and 30 degrees. Leaf margin: Entire. Color: Upper surface: RHS 147A. Lower surface: RHS 187A. Texture: Slightly rough. Thickness: 3.4 mm to 3.7 mm. Venation: Pattern: Parallel. Color of the midvein: Upper surface: RHS 187A. Lower surface: RHS 187B.

Peduncle:
- *Quantity per plant.*—2.
- *Number of flowers per peduncle.*—10 to 13.
- *Length.*—60.0 cm to 65.0 cm.
- *Diameter.*—5.1 mm.
- *Strength.*—Moderate.
- *Aspect.*—Upright.
- *Texture.*—Smooth.
- *Color.*—Dark purple and green (RHS 187A and 148A).
- *Internode length.*—35.0 mm to 45.0 mm.

Inflorescence description:
- *Appearance.*—Upright to slightly pendant, raceme to slightly panicle inflorescence with bilaterally symmetrical flowers that open in succession beginning with the lowermost flower.
- *Inflorescence size.*—Height (from base to tip): 280.0 mm to 330.0 mm. Diameter: 3.8 mm to 4.0 mm.
- *Flowering time.*—First flowers can be expected 10 to 11 months after planting in a 12 cm pot.
- *Flower.*—Height: 75.0 mm to 85.0 mm. Diameter: 85.0 mm to 95.0 mm. Depth of lip: 19.0 mm to 21.0 mm.
- *Flower longevity.*—On the plant: 18 weeks.
- *Fragrance.*—Absent.
- *Petals.*—Arrangement: Open. Shape: Semi-circular. Apex: Obtuse and symmetric. Margin: Entire. Length (from base to tip): 41.0 mm to 44.0 mm. Width: 44.0 mm to 46.0 mm. Color (when fully opened): Main color: Lilac (RHS 76D and 80C). At the base: Lilac (RHS 76D and 80C).
- *Dorsal sepal.*—Shape: Elliptic. Margin: Entire. Length (from base to tip): 41.0 mm to 43.0 mm. Width: 21.0 mm to 23.0 mm. Color (when fully opened): Main color: Lilac (RHS 76D and 80C). At the base: Lilac (RHS 76D and 80C).
- *Lateral sepals.*—Shape: Ovate. Margin: Entire. Length (from base to tip): 42.0 mm to 44.0 mm. Width: 24.0 mm to 26.0 mm. Color (when fully opened): Main color: Lilac (RHS 84C) partially dotted with RHS 59C. At the base: Lilac (RHS 84C) partially dotted with RHS 59C.
- *Labellum* (*lip*).—Margin: Entire. Length: 21.0 mm to 23.0 mm. Width: 25.0 mm to 27.0 mm.
- *Lateral lobe.*—Shape: type V, type of curvature I. Color: Copper striped and dotted (RHS 13D, 180A, 183A and 155D).
- *Apical lobe.*—Shape: Between obdeltoid and rhombic. Color: Copper (RHS 163A) and red-purple (RHS 59B).
- *Callus.*—Color: Yellow (RHS 14A) dotted with dark red (RHS 178A).

Reproductive organs:
- *Arrangement.*—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column.*—Length: 10.0 mm to 11.0 mm. Diameter: 5.5 mm to 6.5 mm. Color: Lilac (RHS 78D).

*Pollinia.*—Quantity: 2. Size: 1.4 mm to 1.6 mm. Color: Orange (RHS 26A).

*Ovary.*—Length: 7.9 mm to 8.1 mm. Diameter: 5.8 mm to 6.0 mm.

*Pedicel.*—Length: 42.0 mm to 44.0 mm. Diameter: 3.7 mm to 4.0 mm.

Disease, pest, and stress resistance: No specific resistance or susceptibility observed.

Temperature tolerance: Tolerant to a low temperature of 15° C. and a high temperature about 30° C.

COMPARISON WITH PARENTAL AND COMMERCIAL VARIETIES

'PHALDANXOK' differs from female parent '07904-0009' (unpatented) in that 'PHALDANXOK' has a copper colored lip, whereas '07904-0009' has an orange colored lip. Additionally, the apical lobe of the lip of 'PHALDANXOK' is shorter than that of '07904-0009' and the callus of the lip of 'PHALDANXOK' is more yellow (RHS 14A), whereas '07904-0009' is more orange (RHS 23A).

'PHALDANXOK' differs from commercial variety 'PHALBOCIQ' (unpatented) in that the apical and lateral lobe of 'PHALDANXOK' is copper, whereas the apical and lateral lobe of 'PHALBOCIQ' is lilac. Additionally, the callus of 'PHALDANXOK' is yellow dotted (RHS 14A and 178A), whereas the callus of 'PHALBOCIQ' is yellow (RHS 5B) and the type of curvature of the lateral lobe of 'PHALDANXOK' is type I, whereas the type of curvature of the lateral lobe of 'PHALBOCIQ' is type III.

I claim:

1. A new and distinct variety of *Phalaenopsis* plant named 'PHALDANXOK' as shown and described herein.

* * * * *